United States Patent [19]

Klingler et al.

[11] Patent Number: 5,658,935
[45] Date of Patent: Aug. 19, 1997

[54] HETEROCYCLES, THEIR PREPARATION AND THEIR USE

[75] Inventors: Otmar Klingler, Rodgau; Gerhard Zoller, Schöneck; Bernd Jablonka, Bad Soden; Melitta Just, Langen; Gerhard Breipohl, Frankfurt am Main; Jochen Knolle, Kriftel; Wolfgang König, Stallwang, all of Germany

[73] Assignee: Hoechst Aktiengesellschaft, Frankfurt am Main, Germany

[21] Appl. No.: 513,897

[22] PCT Filed: Feb. 19, 1994

[86] PCT No.: PCT/EP94/00481

§ 371 Date: Jan. 17, 1996

§ 102(e) Date: Jan. 17, 1996

[87] PCT Pub. No.: WO94/21607

PCT Pub. Date: Sep. 29, 1994

[30] Foreign Application Priority Data

Mar. 13, 1993 [DE] Germany .................. 43 08 034.0

[51] Int. Cl.⁶ .................. A61K 31/40; A61K 31/42; C07D 207/46; C07D 231/34
[52] U.S. Cl. .................. 514/359; 548/132; 548/227; 548/319.5; 548/544; 548/253; 514/364; 514/376; 514/389; 514/425
[58] Field of Search .................. 548/132, 227, 548/319.5, 544, 253; 514/364, 376, 389, 425, 359

[56] References Cited

U.S. PATENT DOCUMENTS

| | | | |
|---|---|---|---|
| 5,389,614 | 2/1995 | Konig et al. | 514/18 |
| 5,397,796 | 3/1995 | Zoller et al. | 514/389 |
| 5,424,293 | 6/1995 | Zoller et al. | 514/20 |

FOREIGN PATENT DOCUMENTS

| | | |
|---|---|---|
| B73653/91 | 2/1993 | Australia . |
| 0126849 | 5/1984 | European Pat. Off. . |
| 0190755 | 6/1985 | European Pat. Off. . |
| 0449079 | 10/1991 | European Pat. Off. . |
| 0512831 | 11/1992 | European Pat. Off. . |
| 0530505 | 3/1993 | European Pat. Off. . |
| 0580008 | 7/1993 | European Pat. Off. . |
| 1539817 | 2/1979 | United Kingdom . |
| 2032419 | 4/1980 | United Kingdom . |

*Primary Examiner*—Jacqueline Haley
*Attorney, Agent, or Firm*—Perman & Green

[57] ABSTRACT

The invention concerns heterocyclic compounds of the general formula (I) in which A, B, R, $R^2$, $R^3$, W, Y, $Z^1$, $Z^2$ and r are as defined in the description, methods of preparing them and their use as inhibitors of thrombocyte aggregation, the metastization of carcinoma cells and the binding of osteoclasts on bone surfaces.

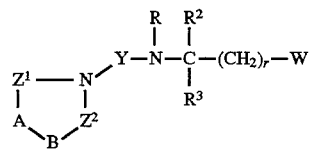

8 Claims, No Drawings

HETEROCYCLES, THEIR PREPARATION AND THEIR USE

This is a national stage application of PCT/EP94/00481 filed Feb. 19, 1994 and published as WO 94/21607.

The present invention relates to substituted heterocycles, their preparation and their use as medicines, in particular as inhibitors of blood platelet aggregation.

EP-A 449 079 and EP-A 530 505 describe hydantoin derivatives which have platelet aggregation-inhibiting effects. EP-A 512 831 describes compounds which prevent fibrinogen binding to blood platelets and, as a result, the aggregation of the platelets. Further investigations showed that the compounds of the present invention are also potent inhibitors of blood platelet aggregation.

The present invention relates to novel heterocycles of the general formula I

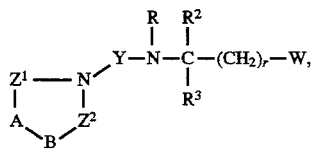

in which $Z^1$ denotes

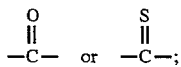

$Z^2$ denotes

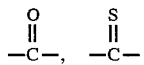

or —$CH_2$—;

Y denotes —$(CH_2)_m CO$—, where m stands for an integer from 1 to 4, or denotes —$CHR^s$—CO— or

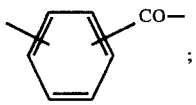

r denotes an integer from 0 to 3;

A denotes —$CHR^1$—, —$NR^1$— or $X^1$—$C_6H_4$—CH=C<;

B denotes —$CH_2$— or —O—;

W denotes —$COW^1$, tetrazolyl, —$SO_2$—OH or —$SO_2NHR^9$;

$W^1$ denotes hydroxyl, ($C_1$–$C_{28}$)-alkoxy, ($C_6$–$C_{14}$)-aryl-($C_1$–$C_8$)-alkoxy, which can also be substituted in the aryl radical, optionally substituted ($C_6$–$C_{14}$)-aryloxy, amino or mono- or di-(($C_1$–$C_{18}$)-alkyl)amino;

R denotes hydrogen or ($C_1$–$C_6$)-alkyl;

$R^1$ denotes

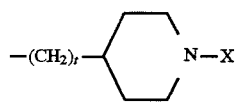

or —$(CH_2)_n$—NH—X or —$(CH_2)_p$—$C_6H_4$—$(CH_2)_q$—NH—X or —$(CH_2)_p$—C(=NX)—$NH_2$ or —$(CH_2)_p$—$C_6H_4$—$(CH_2)_q$—C(=NX)—$NH_2$, in which n stands for a number from 1 to 6, p and q independently of one another stand for a number from 0 to 3 and t stands for a number from 0 to 2, but where, if A denotes —$CHR^1$— or —$NR^1$, B and $Z^2$ denote —$CH_2$—, Y denotes —$(CH_2)_m CO$—, in which m is an integer from 1 to 4, R denotes hydrogen and r is the number 1, then, not at the same time $R^1$ can denote

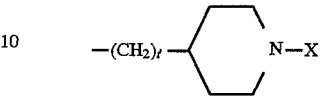

or —$(CH_2)_n$·NH—X or —$(CH_2)_{p'}$—C(=NX)—$NH_2$, in which n' stands for a number from 1 to 4, p' stands for a number from 1 to 3 and t' stands for the numbers 1 or 2;

X denotes hydrogen, ($C_1$–$C_6$)-alkyl, ($C_1$–$C_6$)-alkylcarbonyl, ($C_1$–$C_6$)-alkoxycarbonyl, ($C_1$–$C_{18}$)-alkylcarbonyloxy-($C_1$–$C_6$)-alkoxycarbonyl, optionally substituted ($C_6$–$C_{14}$)-arylcarbonyl, optionally substituted ($C_6$–$C_{14}$)-aryloxycarbonyl, ($C_6$–$C_{14}$)-aryl-($C_1$–$C_6$)-alkoxycarbonyl, which can also be substituted in the aryl radical, cyano, hydroxyl, ($C_1$–$C_6$)-alkoxy or amino or a radical of the formula II $$R'—NH—C(=N—R'')—, \quad (II)$$

where R' and R'' independently of one another stand for hydrogen, ($C_1$–$C_6$)-alkyl, trifluoro-($C_1$–$C_6$)-alkyl, ($C_1$–$C_6$)-alkoxycarbonyl, ($C_1$–$C_6$)-alkylcarbonyl, optionally substituted ($C_6$–$C_{14}$)-arylcarbonyl, ($C_1$–$C_{18}$)-alkylcarbonyloxy-($C_1$–$C_6$)-alkoxycarbonyl, optionally substituted ($C_6$–$C_{14}$)-aryloxycarbonyl, ($C_6$–$C_{14}$)-aryl-($C_1$–$C_6$)-alkoxycarbonyl, which can also be substituted in the aryl radical, cyano, hydroxyl, ($C_1$–$C_6$)-alkoxy or amino;

$X^1$ denotes —$(CH_2)_q$—NH—X or —$(CH_2)_p$—C(=NX)—$NH_2$ in which p and q stand for a number from 0 to 3;

$R^2$ denotes hydrogen, ($C_1$–$C_4$)-alkyl or phenyl, where the ($C_1$–$C_4$)-alkyl and the phenyl can be unsubstituted or mono- or polysubstituted by identical or different radicals from the series hydroxyl, amino, ($C_1$–$C_4$)-alkoxy, imidazolyl, indolyl, pyrrolidinyl, hydroxypyrrolidinyl, phenyl or halogen;

$R^3$ denotes hydrogen, —$COOR^4$, —CO—N($CH_3$)$R^4$ or —CO—NH—$R^4$;

$R^4$ denotes hydrogen or ($C_1$–$C_{28}$)-alkyl, which can optionally be mono- or polysubstituted by identical or different radicals from the series hydroxyl, hydroxycarbonyl, aminocarbonyl, mono- or di-(($C_1$–$C_{18}$)-alkyl)aminocarbonyl, amino-($C_2$–$C_{18}$)-alkylaminocarbonyl, amino-($C_1$–$C_3$)-alkylphenyl-($C_1$–$C_3$)-alkylaminocarbonyl, ($C_1$–$C_{18}$)-alkylcarbonylamino-($C_1$–$C_3$)-alkylphenyl-($C_1$–$C_3$)-alkylaminocarbonyl, ($C_1$–$C_{18}$)-alkylcarbonylamino-($C_2$–$C_{18}$)-alkylaminocarbonyl, ($C_6$–$C_{14}$)-aryl-($C_1$–$C_8$)-alkoxycarbonyl, which can also be substituted in the aryl radical, amino, mercapto, ($C_1$–$C_{18}$)-alkoxy, ($C_1$–$C_{18}$)-alkoxycarbonyl, optionally substituted ($C_3$–$C_8$)-cycloalkyl, halogen, nitro, trifluoromethyl or by the radical $R^5$, where $R^5$ denotes optionally substituted ($C_6$–$C_{14}$)-aryl, ($C_6$–$C_{14}$)-aryl-($C_1$–$C_8$)-alkyl, optionally substituted in the aryl radical, a mono- or bicyclic 5- to 12-membered heterocyclic ring, which can be aromatic, partially hydrogenated or completely hydrogenated and which can contain one, two or three identical or different heteroatoms from the series nitrogen, oxygen and sulphur, a radical $R^6$ or a radical $R^6CO$—, where the aryl and, independently thereof, the heterocyclic radical can be mono- or polysubstituted by identical or different radicals from the series $(C_1-C_{18})$-alkyl, $(C_1-C_{18})$-alkoxy, halogen, nitro, amino or trifluoromethyl;

$R^6$ denotes $-NR^7R^8$, $-OR^7$, $-SR^7$, $-SO_2-OH$, $-SO_2-NHR^9$, tetrazolyl, an amino acid side chain, a natural or unnatural amino acid, imino acid, optionally $N-(C_1-C_8)$-alkylated or $N-((C_6-C_{14})$-aryl-$(C_1-C_8)$-alkylated) azaamino acid radical or a dipeptide radical, which can also be substituted in the aryl radical and/or in which the peptide bond can be reduced to $-NH-CH_2-$, and also their esters and amides, where free functional groups can optionally be replaced by hydrogen or hydroxymethyl or protected by protective groups customary in peptide chemistry;

$R^7$ denotes hydrogen, $(C_1-C_{18})$-alkyl, $(C_6-C_{14}$-aryl-$(C_1-C_8)$-alkyl, $(C_1-C_{18})$-alkylcarbonyl, $(C_1-C_{18})$-alkoxycarbonyl, $(C_6-C_{14})$-arylcarbonyl, $(C_6-C_{14})$-aryl-$(C_1-C_8)$-alkylcarbonyl or $(C_6-C_{14})$-aryl-$(C_1-C_{18})$-alkoxycarbonyl, where the alkyl groups can optionally be substituted by an amino group and/or where the aryl radicals can be mono- or polysubstituted, preferably mono- substituted, by identical or different radicals from the series $(C_1-C_8)$-alkyl, $(C_1-C_{18})$-alkoxy, halogen, nitro, amino and trifluoromethyl, a natural or unnatural amino acid, imino acid, optionally $N-(C_1-C_8)$-alkylated or $N-((C_6-C_{14})$-aryl-$(C_1-C_8)$-alkylated) azaamino acid radical or a dipeptide radical, which can also be substituted in the aryl radical and/or in which the peptide bond can be reduced to $-NH-CH_2-$;

$R^8$ denotes hydrogen, $(C_1-C_{18})$-alkyl, optionally substituted $(C_6-C_{14})$-aryl or $(C_6-C_{14})$-aryl-$(C_1-C_8)$-alkyl, which can also be substituted in the aryl radical;

$R^9$ denotes hydrogen, aminocarbonyl, $(C_1-C_{18})$-alkylaminocarbonyl, $(C_3-C_8)$-cycloalkylaminocarbonyl, $(C_1-C_{18})$-alkyl or $(C_3-C_8)$-cycloalkyl;

$R^S$ denotes an amino acid side chain; and their physiologically tolerable salts.

Cycloalkyl radicals are in particular cyclopropyl, cyclobutyl, cyclopentyl, cyclohexyl, cycloheptyl and cyclooctyl, which, however, can also be substituted by, for example, $(C_1-C_4)$-alkyl. Examples of substituted cycloalkyl radicals are 4-methylcyclohexyl and 2,3-dimethylcyclopentyl.

Alkyl radicals can be straight-chain or branched. This also applies if they carry substituents or occur as substituents of other radicals. Examples of suitable $(C_1-C_{28})$-alkyl radicals are: methyl, ethyl, propyl, butyl, pentyl, hexyl, heptyl, octyl, decyl, undecyl, dodecyl, tridecyl, pentadecyl, hexadecyl, heptadecyl, nonadecyl, eicosyl, docosyl, tricosyl, pentacosyl, hexacosyl, heptacosyl, octacosyl, isopropyl, isopentyl, neopentyl, isohexyl, 3-methylpentyl, 2,3,5-trimethylhexyl, sec-butyl, tert-butyl, tert-pentyl. Preferred alkyl radicals are methyl, ethyl, propyl, isopropyl, butyl, isobutyl, sec-butyl and tert-butyl.

$(C_6-C_{14})$-aryl groups are, for example, phenyl, naphthyl, biphenylyl or fluorenyl, phenyl and naphthyl being preferred. The same applies to radicals such as aralkyl or arylcarbonyl. Aralkyl radicals are in particular benzyl and also 1- and 2-naphthylmethyl, which can also be substituted. Substituted aralkyl radicals are, for example, halobenzyl or $(C_1-C_4)$-alkoxybenzyl.

If phenyl is disubstituted, the substituents can be in the 1,2-, 1,3- or 1,4-position relative to one another. The 1,3- and the 1,4-positions are preferred.

Mono- or bicyclic 5- to 12-membered heterocyclic rings are, for example, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl or a benzo-fused or cyclopenta-, cyclohexa- or cyclohepta-fused derivative of these radicals.

These heterocycles can be substituted on one nitrogen atom by $(C_1-C_7)$-alkyl, e.g. methyl or ethyl, phenyl or phenyl-$(C_1-C_4)$-alkyl, e.g. benzyl and/or on one or more carbon atoms by $(C_1-C_4)$-alkyl, halogen, hydroxyl, $(C_1-C_4)$-alkoxy, e.g. methoxy, phenyl-$(C_1-C_4)$-alkoxy, e.g. benzyloxy, or oxo and can be aromatic or partially or completely saturated. Nitrogen heterocycles can also be present as N-oxides.

Radicals of this type, are, for example, 2- or 3-pyrrolyl, phenylpyrrolyl, e.g. 4- or 5-phenyl-2-pyrrolyl, 2-furyl, 2-thienyl, 4-imidazolyl, methylimidazolyl, e.g. 1-methyl-2-, 4- or 5-imidazolyl, 1,3-thiazol-2-yl, 2-, 3- or 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, e.g. 1-methyl-, 5-methyl-, 5-methoxy-, 5-benzyloxy-, 5-chloro- or 4,5-dimethyl-2-indolyl, 1-benzyl-2- or 3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl. Partially hydrogenated or completely hydrogenated heterocyclic rings are, for example, dihydropyridinyl, pyrrolidinyl, e.g. 2-, 3- or 4-(N-methylpyrrolidinyl), piperazinyl, morpholinyl, thiomorpholinyl, tetrahydrothienyl or benzodioxolanyl.

Halogen stands for fluorine, chlorine, bromine or iodine, in particular for fluorine or chlorine.

Natural and unnatural amino acids can be present, if chiral, in the D- or L-form. α-Amino acids are preferred. Examples which may be mentioned (cf. Houben-Weyl, Methoden der organischen Chemie [Methods of Organic Chemistry], Volume XV/1 and 2, Stuttgart, 1974) are:

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr Thy, Tbx, Tia, Tle, Tly, Trp, Trta, Tyr, Val, Tbg, Npg, Chg, Cha, Thia, 2,2-diphenylaminoacetic acid, 2-(p-tolyl)-2-phenylaminoacetic acid, 2-(p-chlorophenyl)aminoacetic acid.

Amino acid side chains are understood as meaning side chains of natural or unnatural amino acids. Azaamino acids are natural or unnatural amino acids in which the central component

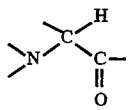

is replaced by

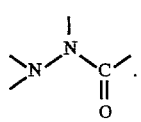

Suitable radicals of an imino acid are in particular radicals of heterocycles from the following group: pyrrolidine-2-carboxylic acid; piperidine-2-carboxylic acid; tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo-[3.1.0] hexane-3-carboxylic acid; 2-azospiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro (bicyclo[2.2.2]octane)-2,3-pyrrolidine-5-carboxylic acid; 2-azatricyclo[4.3.0.1.$^{6,9}$]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine- 3-carboxylic acid; hydroxypyrrolidine-2-carboxylic acid; which all can be optionally substituted (see following formulae):

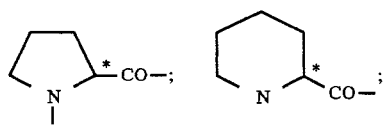

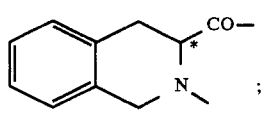

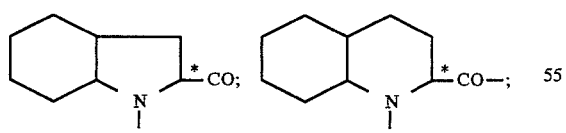

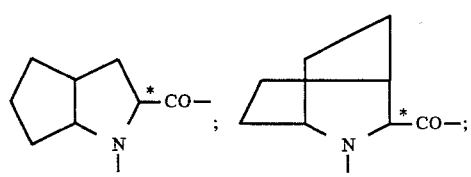

-continued

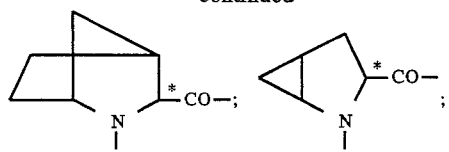

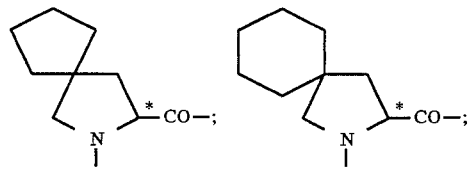

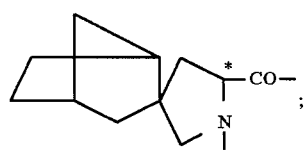

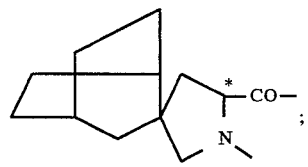

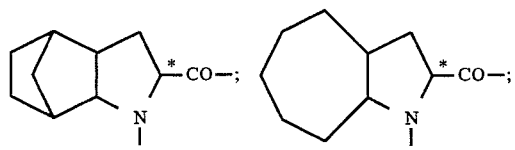

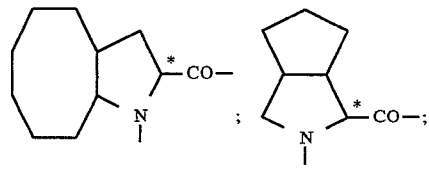

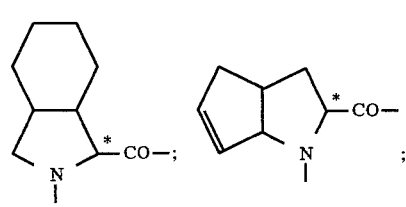

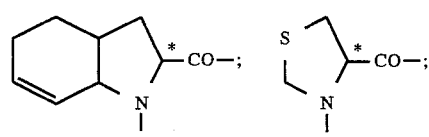

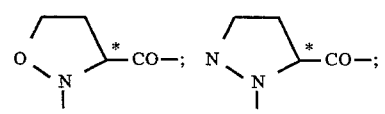

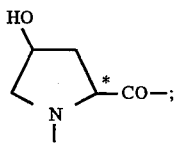

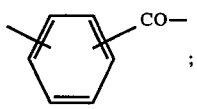

r stands for 1;

W denotes —COW$^1$;

Z$^2$ denotes

W$^1$ denotes hydroxyl, (C$_1$–C$_4$)-alkoxy, in particular methoxy, ethoxy, 2-propyloxy, isobutyloxy or tert-butyloxy, or benzyloxy;

R denotes hydrogen;

R$^1$ denotes —(CH$_2$)$_n$—NH—X, where n stands for an integer from 1 to 5, —(CH$_2$)$_p$—C$_6$H$_4$—(CH$_2$)$_q$—NH—X or —(CH$_2$)$_p$—C$_6$H$_4$—(CH$_2$)$_q$—C(=NX)—NH$_2$, where p and q independently of one another stand for 0 or 1;

X denotes hydrogen, (C$_1$–C$_6$)-alkoxycarbonyl, (C$_1$–C$_6$)-alkylcarbonyl, ($_1$–C$_{18}$)-alkylcarbonyloxy-(C$_1$–C$_6$)-alkoxycarbonyl, (C$_6$–C$_{14}$)-aryl-(C$_1$–C$_6$)-alkoxycarbonyl or a radical of the fomula

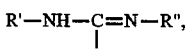

in which R' and R" independently of one another stand for hydrogen, trifluoroethyl, (C$_1$–C$_6$)-alkylcarbonyl, (C$_1$–C$_6$)-alkoxycarbonyl, (C$_1$–C$_{18}$)-alkylcarbonyloxy-(C$_1$–C$_6$)-alkoxycarbonyl or (C$_6$–C$_{14}$)-aryl-(C$_1$–C$_6$)-alkoxycarbonyl;

X$^1$ denotes —(CH$_2$)$_q$—NH—X or —C(=NX)—NH$_2$, where q stands for 0 or 1;

R$^2$ denotes hydrogen;

R$^3$ denotes —CO—NH—R$^4$, where —NH—R$^4$ stands for the radical of an α-amino acid, its ω-amino-(C$_2$–C$_8$)-alkylamide or its (C$_1$–C$_8$)-alkyl or benzyl ester, or where R$^4$ denotes methyl which is substituted by an amino acid side chain and by a radical from the series —SO$_2$—OH, —SO$_2$—NHR$^9$ and tetrazolyl.

Radicals of α-amino acids standing for —NH—R$^4$ are in this case particularly preferably the valine, lysine, phenylalanine, phenylglycine or 4-chlorophenylglycine radical. If —NH—R$^4$ in this case stands for an ester of one of these α-amino acids, the methyl, ethyl, isopropyl, isobutyl, tert-butyl ester or benzyl ester is preferred.

The heterocycles on which the abovementioned radicals are based are disclosed, for example, in U.S. Pat. Nos. 4,344,949; 4,374,847; 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

Dipeptides can contain natural or unnatural amino acids, imino acids and also azaamino acids as components. Furthermore, the natural or unnatural amino acids, imino acids, azaamino acids and dipeptides can also be present as esters or amides, such as e.g. methyl ester, ethyl ester, isopropyl ester, isobutyl ester, tert-butyl ester, benzyl ester, ethylamide, semicarbazide or ω-amino-(C$_4$–C$_8$)-alkylamide.

Functional groups of the amino acids, imino acids and dipeptides can be present in protected form. Suitable protective groups such as e.g. urethane protective groups, carboxyl protective groups and side chain protective groups are described in Hubbuch, Kontakte (Merck) 1979, No. 3, pages 14 to 23 and in Büllesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, Z(NO$_2$), Z(Hal$_n$), Bobz, Iboc, Adpoc, Mboc, Acm, tert-butyl, OBzl, ONbzl, OMbzl, Bzl, Mob, Pic, Trt.

Physiologically tolerable salts of the compounds of the general formula I are in particular pharmaceutically utilizable or non-toxic salts.

Such salts are formed, for example, from compounds of the general formula I which contain acidic group, e.g. carboxyl, with alkali metals or alkaline earth metals, such as e.g. Na, K, Mg and Ca, and also with physiologically tolerable organic amines, such as e.g. triethylamine, ethanolamine or tris(2-hydroxyethyl)amine.

Compounds of the general formula I which contain basic groups, e.g. an amino group, an amidino group or a guanidino group, form salts with inorganic acids, such as e.g. hydrochloric acid, sulphuric acid or phosphoric acid and with organic carboxylic or sulphonic acid, such as e.g. acetic acid, citric acid, benzoic acid, maleic acid, fumaric acid, tartaric acid, methanesulphonic acid or p-toluenesulphonic acid.

The compounds of the general formula I according to the invention can contain optically active carbon atoms and can thus be present in the form of pure enantiomers or in the form of enantiomer mixtures. Both pure enantiomers and enantiomer mixtures and also diastereomers and diastereomer mixtures are a subject of the present invention.

The compounds of the general formula I according to the invention can moreover contain mobile hydrogen atoms, i.e. can be present in various tautomeric forms. These tautomers are also a subject of the present invention.

Preferred compounds of the formula I are those in which Y denotes —(CH$_2$)$_m$CO—, where m stands for 1 or 2, or —CHR$^s$CO where R$^s$ stands for the side chain of the amino acids alanine, valine, phenylalanine, tyrosine, leucine, isoleucine, tryptophan, lysine, histidine, asparagine, glutamine or phenylglycine, or Compounds of the formula I can be prepared by fragment condensation of a compound of the general formula III

with a compound of the general formula IV

where the radicals Z$^1$, Z$^2$, A, B, R, R$^2$, R$^3$, Y and W and also r are defined as indicated above.

The starting compounds of the general formula IV are as a rule synthesized stepwise from the C-terminal end. For condensation of the compounds of the general formula III with those of the general formula IV, the coupling methods of peptide chemistry known per se (see e.g. Houben-Weyl, Methoden der organischen Chemie [Methods of Organic Chemistry], Volumes 15/1 and 15/2, Stuttgart, 1974) are advantageously used. For this coupling, it is as a rule necessary that amino groups contained in $R^1$, $R^3$ and W are protected by reversible protective groups during the condensation. The same applies to the carboxyl groups of the compounds of the formula IV, which are preferably present as ($C_1$-$C_6$)-alkyl, benzyl or tert-butyl esters. Amino group protection is unnecessary if the amino groups to be generated are still present as nitro or cyano groups and are only formed, after coupling, by hydrogenation. After coupling, the protective groups present are removed in a suitable manner. For example, $NO_2$ groups (guanidino protection), benzyloxycarbonyl groups and benzyl esters can be removed by hydrogenation. The protective groups of the tert-butyl type are cleaved by acid, while the 9-fluorenylmethyloxycarbonyl radical is removed by means of secondary amines.

The starting compounds of the general formula III can be obtained, if A stands for —$CHR^1$— and B stands for —$CH_2$— and $Z^1$ and $Z^2$ stand for —CO—, as follows:

By reaction of succinic acid derivatives of the general formula V or their esters

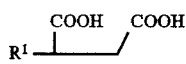

or of ethanetricarboxylic acid derivatives of the general formula Va or their esters, where $R^1$ is defined as indicated above,

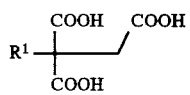

with amino acids of the general formula VI or preferably their methyl, ethyl, benzyl or tert-butyl esters,

where Y is defined as indicated above (see e.g. Houben-Weyl, Methoden der organischen Chemie [Methods of Organic Chemistry], Volume 11/2 and E5).

The starting compounds of the general formula III can be obtained, if A stands for —$NR^1$— and B stands for oxygen and $Z^1$ and $Z^2$ stand for —CO— or —CS—, as follows:

By reaction of hydroxylamine derivatives of the general formula VII, where $R^1$ is defined as indicated above,

with an isocyanato or isothiocyanato ester of the general formula VIII, where $Z^1$ and Y are defined as indicated above,

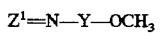

hydroxyurea derivatives of the general formula IX

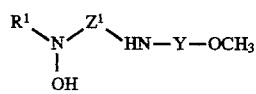

are obtained which are cyclized by reaction with phosgene or thiophosgene and by subsequent hydrolysis of the ester functions yield the compounds of the general formula IIIa

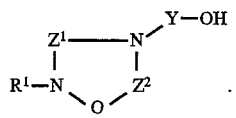

During the cyclization, guanidino groups can be protected by protective groups, such as $NO_2$ or Mtr. Amino groups or amidino groups in the side chain must also be present in protected form (for example as the Boc or Z derivative) or further as the $NO_2$ or cyano function, which can later be reduced to the amino group or, in the case of the cyano group, also converted into the amidino group.

The starting compounds of the general formula III can be obtained, if A stands for —$CHR^1$—, B stands for oxygen and $Z^1$ and $Z^2$ stand for —CO—, by reaction of compounds of the general formula X

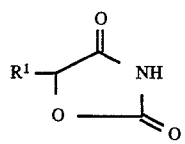

which can be prepared by processes known from the literature (see e.g. J. W. Clarke-Lewis, Chem. Rev. 58 (1958), 63; R. L. Dow et al., J. Med. Chem. 34 (1991), 1538 and literature cited there; EP-A 428 312), with compounds of the general formula XI

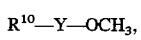

where $R^1$ and Y are defined as indicated above and $R^{10}$ represents a suitable leaving group, and subsequent hydrolysis of the ester functions.

The starting compounds of the general formula III can be obtained, if A stands for —$NR^1$— and B stands for —$CH_2$— and $Z^1$ stands for —CO— and $Z^2$ stands for —CO—, as follows:

By reaction of compounds of the general formula XII

where $R^1$ is defined as indicated above, with glyoxylic acid or its esters, compounds of the general formula XIII

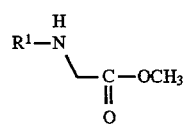

are obtained, for example, under the conditions of reductive amination.

By reaction of the compounds of the general formula XIII with an isocyanato or an isothiocyanatocarboxylic acid ester, for example of the general formula VIII, or of a corresponding carboxylic acid, urea derivatives, for example of the general formula XIV

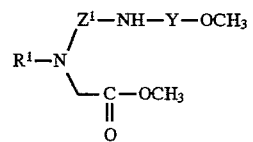

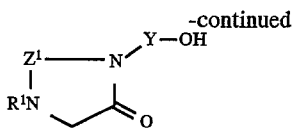 (IIIb)

are obtained which can be cyclized and hydrolysed to give compounds of the general formula IIIb.

The starting compounds of the general formula III can be obtained, if A stands for —CHR$^1$— and B stands for —CH$_2$— and Z$^1$ stands for —CO— and Z$^2$ stands for —CH$_2$—, as follows:

By N-alkylation of compounds of the general formula XV

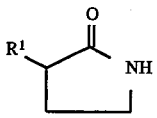 (XV)

with compounds of the general formula XI, where the compounds of the general formula XV are obtainable by C-alkylation of 2-pyrrolidinone protected on the nitrogen, with compounds of the general formula XVI $$R^1 - R^{10}, \quad (XVI)$$

in which R$^{10}$ represents a suitable leaving group. Corresponding alkylation reactions of pyrrolidinones are described, for example, in M. A. E. Bowman et al., Org. Prep. Proced. Int. 22 (1990) 636; C. H. Kochbar et al., J. Org. Chem. 50 (1985) 3019; J. D. Stewart et al., J. Org. Chem. 52 (1987) 2113; T. J. Hagen, Synlett (1990) 63.

The starting compounds of the general formula III can be obtained, if A stands for —NR$^1$— and B stands for —CH$_2$— and Z$^1$ stands for —CO— or —CS— and Z$^2$ stands for —CH$_2$—, as follows:

By cyclization of compounds of the general formula XVII

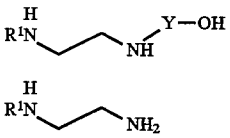

(XVII)

(XVIII)

or, for example, of their esters with phosgene or thiophosgene or synthesis equivalents of phosgene or thiophosgene, compounds of the general formula XVII being obtainable, for example, from compounds of the general formula XVIII by a reductive amination (see e.g. W. S. Saari et al., J. Med. Chem. 33 (1990), 2590). Alternatively, compounds of the general formula III, in which A stands for —NR$^1$— and B stands for —CH$_2$— and Z$^1$ stands for —CO— and Z$^2$ stands for —CH$_2$—, are obtained by successive N-alkylation of the compound of the formula XIX

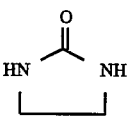 (XIX)

with compounds of the general formula XI and compounds of the general formula XVI.

The starting compounds of the general formula III can be obtained, if A stands for X$^1$—C$_6$H$_4$—CH=C<, by condensation of compounds of the general formula XX

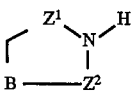 (XX)

$$X^1 - C_6H_4 - CHO \quad (XXI)$$

with the benzaldehydes of the general formula XXI and subsequent alkylation with compounds of the general formula XI.

In all reaction steps, functional groups which may be free must be protected by suitable reversible protective groups, which are later removed again in a suitable manner.

For the guanylation and nitroguanylation of the amino compounds the following reagents can be used:

1. O-Methylisourea (S. Weiss and H. Krommer, Chemiker Zeitung 98 (1974) 17–618),
2. S-Methylisothiourea R. F. Borne, M. L. Forrester and I. W. Waters, J. Med. Chem. 20 (1977) 771–776),
3. Nitro-S-Methylisothiourea (L. S. Hafner and R. E. Evans, J. Org. Chem. 24 (1959) 1157),
4. Formamidinesulphonic acid (K. Kim, Y.-T. Lin and H. S. Mosher, Tetrahedron Lett. 29 (1988) 3183–3186),
5. 3,5-Dimethyl-1-pyrazolylformamidinium nitrate. (F. L. Scott, D. G. O'Donovan and J. Reilly, J, Amer. Chem. Soc. 75 (1953) 4053–4054),
6. N,N'-Di-tert-butyloxycarbonyl-S-methylisothiourea (R. J. Bergeron and J. S. McManis, J. Org. Chem. 52 (1987) 700–1703),
7. N-Alkoxycarbonyl-, N,N'-dialkoxycarbonyl-, N-alkylcarbonyl- and N,N'-dialkylcarbonyl-S-methylisothiourea (H. Wollweber, H. Köing, E. Niemers, A. Widding, P. Andrews, H.-P. Schulz and H. Thomas, Arzneim. Forsch./Drug Res. 34 (1984) 531–542).

Amidines can be prepared from the corresponding cyano compounds by addition of alcohols (e.g. methanol or ethanol) in acidic anhydrous medium (e.g. dioxane, methanol or ethanol) and subsequent aminolysis (G. Wagner, P. Richter and Ch. Garbs, Pharmazie 29 (1974) 12–15). A further method of preparing amidines is the addition of H$_2$S to the cyano group, followed by a methylation of the resulting thioamide and subsequent reaction with ammonia (GDR patent no. 235 866).

The compounds of the general formula I and their physiologically tolerable salts can be administered as medicines per se, in mixtures with one another or in the form of pharmaceutical preparations which permit enteral or parenteral administration and which contain as active constituent an effective dose of at least one compound of the general formula I or of a salt thereof, in addition to customary pharmaceutically innocuous excipients and additives. The preparations normally contain about 0.5 to 90% by weight of the therapeutically active compound.

The medicines can be administered orally, e.g. in the form of pills, tablets, lacquered tablets, sugar-coated tablets, granules, hard and soft gelatine capsules, solutions, syrups, emulsions or suspensions or aerosol mixtures. However, administration can also be carried out rectally, e.g. in the form of suppositories, or parenterally, e.g. in the form of injection or infusion solutions or microcapsules, percutaneously, e.g. in the form of ointments or tinctures, or nasally, e.g. in the form of nasal sprays.

The pharmaceutical preparations are prepared in a manner known per se, pharmaceutically inert inorganic or organic excipients being used. For the preparation of pills, tablets, sugar-coated tablets and hard gelatine capsules, use can be made of e.g. lactose, maize starch or derivatives thereof, talc, stearic acid or its salts, etc. Excipients for soft gelatine capsules and suppositories are e.g. fats, waxes, semi-solid and liquid polyols, natural or hardened oils etc. Suitable excipients for the preparation of solutions and syrups are e.g. water, sucrose, invert sugar, glucose, polyols etc. Suitable excipients for the preparation of injection solutions are water, alcohols, glycerol, polyols, vegetable oils etc. Suitable excipients for microcapsules or implants are copolymers of glycolic acid and lactic acid.

Besides the active compounds and excipients, the pharmaceutical preparations can also contain additives, such as e.g. fillers, extenders, disintegrants, binders, lubricants, wetting agents, stabilizers, emulsifiers, preservatives, sweeteners, colourants, flayoutings or aromatizers, thickeners, diluents, buffering substances, and further solvents or solubilizers or agents for achieving a depot effect, and also salts for changing the osmotic pressure, coating compositions or antioxidants. They can also contain two or more compounds of the general formula I or their pharmacologically acceptable salts and additionally one or more other therapeutically active substances.

Other therapeutically active substances of this type are, for example, circulation-promoting agents, such as dihydroergocristine, nicergoline, buphenine, nicotinic acid and its esters, pyridylcarbinol, bencyclan, cinnarizine, naftidrofuryl, raubasine and vincamine; positively inotropic compounds, such as digoxin, acetyldigoxin, metildigoxin and lanatoglycosides; coronary dilators, such as carbochromen; dipyridamol, nifedipine and perhexiline; antianginal compounds, such as isosorbide dinitrate, isosorbide mononitrate, glycerol nitrate, molsidomin and verapamil; β-blockers, such as propranolol, oxprenolol, atenolol, metoprolol and penbutolol. Moreover, the compounds can also be combined, for example, with nootropically active substances, such as e.g. piracetam, or CNS-active substances, such as pirlindol, sulpiride etc.

The dose can vary within wide limits and is to be suited to the individual conditions in each individual case. In general, in the case of oral administration a daily dose of about 0.1 to 1 mg/kg, preferably 0.3 to 0.5 mg/kg, of body weight is appropriate to achieve effective results, in the case of intravenous administration, the daily dose is in general about 0.01 to 0.3 mg/kg, preferably 0.05 to 0.1 mg/kg, of body weight.

The daily dose can be divided, in particular in the case of the administration of relatively large amounts, into several, e.g. 2, 3 or 4, part administrations. If appropriate, depending on individual behaviour, it may be necessary to deviate upwards or downwards from the daily dose indicated. Pharmaceutical preparations normally contain 0.2 to 50 mg, preferably 0.5 to 10 mg, of active compound of the general formula I or of one of its pharmaceutically acceptable salts per dose.

The novel heterocycles of the formula I according to the invention have the ability to inhibit the binding of fibrinogen, fibronectin and the von Willebrand factors to integrin receptors. In this manner, they affect the cell-cell and cell-matrix interaction and can thus prevent the formation of blood platelet thrombi. Integrins are cell membrane glycoproteins and mediate cell adhesion by interaction with a plurality of extra-cellular proteins such as fibronectin, laminin, collagen, vitronectin, and von Willebrand factor or with other cell membrane proteins such as e.g. ICAM-1. An important receptor from the integrin family is the glycoprotein IIb/IIIa localized on blood platelets (fibrinogen receptor)—a key protein of platelet-platelet interaction and thrombus formation. A central fragment in the receptor recognition sequence of these proteins is the tripeptide Arg-Gly-Asp (E. Ruoslahti and M. D. Pierschbacher, Science 238 (1987) 491–497; D. R. Phillips, I. F. Charo, L. V. Parise and L. A. Fitzgerald, Blood 71 (1988) 831–843).

The heterocycles of the general formula I therefore find an application for the prophylaxis and therapy of arterial vascular disorders such as acute myocardial infarct in combination with lysis therapy, post-infarct treatment, secondary prevention of myocardial infarct, reocclusion prophylaxis after lysis and dilatation, unstable angina pectoris, transitory ischaemic attacks, stroke, coronary bypass operation and reocclusion prophylaxis of the bypass, pulmonary embolism, peripheral arterial occlusive diseases, disseminating aneurysms, for the therapy of venous and microcirculatory vascular disorders such as deep vein thrombosis, disseminated intravascular clotting, post-operative and post-partum trauma, surgical or infectious shock, septicaemia, for the therapy in disorders with hyperreactive platelets, thrombotic thrombocytopenic purpura, preeclampsia, premenstrual syndrome, dialysis, extracorporal circulation; a further application is provided in inflammations and in the treatment of tumours. Osteoporosis can further be prevented by inhibition of osteoclast binding to the bone surface.

The compounds are tested in particular for their inhibitory effect on blood platelet aggregation and the adhesion of fibrinogen to blood platelets. Gel-filtered blood platelets from human donor blood are used, which are activated with ADP or thrombin.

The inhibition of the binding of fibrinogen to its receptor (glycoprotein IIb/IIIa) on intact, gel-filtered human platelets by the compounds according to the invention is tested. The $K_i$ value of the inhibition of binding of $^{125}$I-fibrinogen after stimulation with ADP (10 μM) is indicated. (Reference: J. S. Bennett and G. Vilaire, J. Clin. Invest. 64 (1979) 1393–1401; E. Kornecki et al., J. Biol. Chem. 256 (1981), 5695–5701; G. A. Marguerie et al., J. Biol. Chem. 254 (1979) 5357–5363; G. A. Marguerie et al., J. Biol. Chem. 255 (1980) 154–161.)

As a functional test, the inhibition of the aggregation of gel-filtered human platelets is measured after ADP or thrombin stimulation by the compounds according to the invention. The $IC_{50}$ value of the inhibition is indicated (reference: G. A. Marguerie et al., J. Biol. Chem. 254 (1979), 5357–5363).

On testing of the inhibition of fibrinogen binding and the inhibition of aggregation, the following results are obtained for the compounds of the examples which follow:

| Example | Inhibition of platelet aggregation | | Inhibition of fibrinogen binding |
|---|---|---|---|
| | ADP (μM) | thrombin (μM) | $K_i$ (μM) |
| 1 | 0.2 | 0.09 | 0.043 |
| 12 | 100 | 80 | |
| 13 | 100 | 100 | |
| 17 | 100 | 100 | |
| 18 | 100 | 70 | |
| 14 | 20 | 35 | |
| 15 | 200 | 200 | |
| 16 | 20 | 9 | |
| 19 | 4 | 1 | |

EXAMPLES

Example 1

{3-[4-(Aminoiminomethyl)benzyl]-2,5-dioxopyrrolidin-1-yl}acetyl-L-aspartyl-L-phenylglycine a) Synthesis of ethyl 4-(4-cyanobenzyl)-3,3-bisethoxycarbonylbutyrate 24.6 g of ethyl 1,1,2-ethanetricarboxylate are dissolved in 500 ml of abs. ethanol and treated in portions with 11.2 g of potassium tert-butoxide. 19.6 g of p-bromomethylbenzonitrile are added in portions to this mixture. It is heated at about 60° C. for 5 hours. It is then allowed to cool to room temperature, the precipitate is filtered off and the filtrate is concentrated in vacuo. The oily residue which remains is chromatographed on silica gel using dichloromethane/methanol/water/acetic acid (100:1 (100:10:1:1). The product fractions are combined and concentrated to dryness in vacuo. An oil remains which slowly crystallizes.

Yield: 28.7 g

MS(CI): 362 [M+H]$^+$

NMR(CDCl$_3$): $\delta$=1.25 ppm (m, 9H); 2.82 ppm (s, 2H); 3.45 ppm (s, 2H); 4.20 ppm (m, 6H); 7.25 ppm (d, 2H); 7.55 ppm (d, 2H).

b) Synthesis of ethyl 4-[4-(aminoiminomethyl)benzyl]-3,3-bisethoxycarbonylbutyrate hydrochloride 28.7 g of ethyl 4-(4-cyanobenzyl)-3,3-bisethoxycarbonylbutyrate are dissolved in 900 ml of abs. ethanol and cooled to −5° C. in a dry-ice bath. Dry HCl gas is introduced into this solution, the temperature always being kept below 0° C. After about 4 h, the strongly exothermic reaction subsides and the reaction mixture is allowed to stand overnight at 0° C. The solvent is then stripped off in vacuo in a rotary evaporator and the oily residue is dissolved in 200 ml of dry isopropanol and cautiously treated with NH$_3$/isopropanol until the mixture has reached pH 8. The mixture is stirred at 60°–70° C. for 3 h and allowed to stand overnight at room temperature. The cooled solution is filtered and the filtrate is concentrated in vacuo and the oily residue is triturated with diethyl ether. The solid precipitate is filtered off with suction and washed with diethyl ether. After drying in a desiccator 25.47 g remain.

MS(FAB): 379.2 [M+H]$^+$

NMR(CDC$_{13}$): $\delta$=1.25 ppm (m, 9H); 2.75 ppm (s, 2H); 3.40 ppm (s, 2H); 4.18 ppm (m, 6H); 7.28 ppm (d, 2H); 7.88 ppm (d, 2H); 8.43 ppm (br s, 2H); ppm (br s, 2H). 9.33 (br s, 2H).

c) Synthesis of 4-[4-(aminoiminomethyl)benzyl]-3,3-bisethoxycarbonylbutyric acid hydrochloride 11.34 g of ethyl 4-[4-(aminoiminomethyl)benzyl]-3,3-bisethoxycarbonylbutyrate hydrochloride are stirred in 250 ml of 6N HCl at 40° C. for 1 h and at 80° C. for 2 h. The mixture is then allowed to stand overnight at room temperature and is concentrated to dryness in vacuo. The residue is taken up in a little water and freeze-dried.

Yield: 10.5 g

MS (FAB): 351.2 [M+H]$^+$ d) Synthesis of {4-[4-(aminoiminomethyl)benzyl]-3,3-bisethoxycarbonylbutyryl}glycine methyl ester hydrochloride 10.5 g of 4-[4-(aminoiminomethyl)benzyl]-3,3-bisethoxycarbonylbutyric acid hydrochloride are dissolved in 500 ml of dimethylformamide. 3.75 g of glycine methyl ester hydrochloride, 9.83 g of O-[(cyanoethoxycarbonylmethylene)amino]-N,N,N',N'-tetramethyluronium tetrafluoroborate (TOTU) and 11.5 ml of N-ethylmorpholine are then added successively. The mixture is stirred for 24 h and the solvent is then stripped off in vacuo. The oily residue is chromatographed on silica gel using dichloromethane/methanol/water/acetic acid (100:10:1:1). The fractions containing the product are combined and concentrated.

Yield: 7.8 g

MS(FAB): 442.2 e) Synthesis of {3-[4-(aminoiminomethyl)benzyl]-2,5-dioxopyrrolidin-1-yl}acetic acid hydrochloride 4 g of {4-[4-(aminoiminomethyl)benzyl]-3,3-bisethoxycarbonylbutyryl}glycine methyl ester hydrochloride are heated under reflux in 100 ml of conc. HCl for 30 min, then the mixture is concentrated to dryness in vacuo, and the residue is redistilled twice with 10 ml of water and dried in a high vacuum.

Yield: 3 g

MS(FAB): 290.1 [M+H]$^+$ f) Synthesis of {3-[4-(aminoiminomethyl)benzyl]-2,5-dioxopyrrolidin-1-yl} acetyl-L-($\beta$-tert-butyl)aspartyl-L-phenylglycine tert-butyl ester 1.74 g of {3-[4-(aminoiminomethyl)benzyl]-2,5-dioxopyrrolidin-1-yl}acetic acid hydrochloride are dissolved in 120 ml of DMF and treated successively with 2.49 g of H-Asp(OtBu)-Phg-OtBu, 2.95 g of TOTU and 3.45 ml of N-ethylmorpholine. The mixture is stirred for 24 h and then concentrated to dryness. The oily residue which remains is chromatographed on silica gel using dichloromethane/methanol/water/acetic acid (100:10:1:1). The combined substance-containing fractions are concentrated. 0.98 g remains.

MS(FAB): 650.3 [M+H]$^+$ g) Synthesis of {3-[4-(aminoiminomethyl)benzyl]-2,5-dioxopyrrolidin-1-yl}acetyl-L-aspartyl-L-phenylglycine 980 mg of {3-[4-(aminoiminomethyl)benzyl]-2,5-dioxopyrrolidin-1-yl}acetyl-L-($\beta$-tert-butyl)aspartyl-L-phenylglycine tert-butyl ester are treated with 20 ml of trifluoroacetic acid and, after allowing to stand for 20 min, the mixture is concentrated to dryness. The residue is redistilled three times with some diethyl ether, then taken up in a little water and freeze-dried.

Yield: 398 mg

MS(FAB): 538.2 [M+H]$^+$ $^1$H-NMR (D$_2$O): $\delta$=2.51–3.51 ppm (m, 8H); 4.10–4.35 ppm (m, 2H); 5.45 (d, 1H); 7.30–7.80 ppm (m, 9H)

Amino acid analysis: Asp: 0.99 (1); Gly: 1.00 (1); Phg: 1.01 (1).

The following are obtained analogously:

Example 2

{3-[4-(Aminoiminomethyl)benzyl]-2,5-dioxopyrrolidin-1-yl}acetyl-L-aspartyl-L-phenylalanine Example 3

{3-[4-(Aminoiminomethyl)benzyl]-2,5-dioxopyrrolidin-1-yl}acetyl-L-aspartyl-L-valine Example 4

{3-[4-(Aminoiminomethyl)phenyl]-2,5-dioxopyrrolidin-1-yl}acetyl-L-aspartyl-L-phenylglycine Example 5

2-{3-[4-(Aminoiminomethyl)benzyl]-2,5-dioxopyrrolidin-1-yl}-propionyl-L-aspartyl-L-phenylglycine Example 6

{2-[4-(Aminoiminomethyl)benzyl]-3,5-dioxo[1,2,4]oxadiazolidin-4-yl}acetyl-L-aspartyl-L-phenylglycine

Example 7

{5-[4-(Aminoiminomethyl)benzyl]-2,4-dioxo[1,3]
oxazolidin-3-yl}-acetyl-L-aspartyl-L-phenylglycine

Example 8

{3-[4-(Aminoiminomethyl)phenyl]-2,5-dioxoimidazolidin-
1-yl}-acetyl-L-aspartyl-L-phenylglycine

Example 9

[3-(3-Guanidinopropyl)-2,5-dioxopyrrolidin-1-yl]acetyl-L-
aspartyl-L-phenylglycine

Example 10

3-[3-(3-Aminopropyl)-2,5-dioxopyrrolidin-1-yl]benzoyl-L-
aspartyl-L-phenylglycine

Example 11

<{{3-[4-(Amlnoiminomethyl)benzyl]-2,5-dioxopyrrolidin-
1-yl}-acetyl-L-aspartylamido}phenylmethylsulfonyl>urea

Example 12

{3-[4-(Aminoiminomethyl)benzyl]-2,5-dioxopyrrolidin-1-
yl}acetyl-L-tryptophan methyl ester 403 mg of {3-[4-(aminoiminomethyl)benzyl]-2,5-
dioxopyrrolidin-1-yl}acetic acid hydrochloride are coupled
with 356.6 mg of L-tryptophan methyl ester hydrochloride
by the process described above. After working up and
chromatographic purification, 270 mg of {3-[4-
(aminoiminomethyl)benzyl]-2,5-dioxopyrrolidin-1-
yl}acetyl-L-tryptophan methyl ester are obtained.

MS (FAB): 490.2 [M+H]$^+$

Example 13

{3-[4-(Aminoiminomethyl)benzyl]-2,5-
dioxopyrrolidin-1-yl}acetyl-D,L-homophenylalanine
methyl ester 403 mg of {3-[4-(aminoiminomethyl)benzyl]-2,5-
dioxopyrrolidin-1-yl}acetic acid hydrochloride are coupled
with 270 mg of D,L-homophenylalanine methyl ester by the
process described above. After working up and chromato-
graphic purification, 343 mg of {3-[4-(aminoiminomethyl)
benzyl]-2,5-dioxopyrrolidin-1-yl}-acetyl-D,L-
homophenylalanine methyl ester are obtained.

MS(FAB): 465.2 [M+H]$^+$

Example 14

{3-[4-(Aminoiminomethyl)benzyl]-2,5-
dioxopyrrolidin-1-yl}acetyl-L-(β-isopropyl)aspartyl-
L-phenylglycine isopropyl ester 412 mg of {3-[4-(aminoiminomethyl)benzyl]-2,5-
dioxopyrrolidin-1-yl}acetic acid hydrochloride are coupled
with 500 mg of L-(β-isopropyl)aspartyl-L-phenylglycine
isopropyl ester by the process described above. After work-
ing up and chromatographic purification, 330 mg of {3-[4-
(aminoiminomethyl)benzyl]-2,5-dioxopyrrolidin-1-
yl}acetyl-L-(β-isopropyl)aspartyl-L-phenylglycine
isopropyl ester are obtained.

MS(FAB): 622.4 [M+H]$^+$

Example 15

Methyl 3-(R,S)-3-<{3-[4-(aminoiminomethyl)
benzyl]-2,5-dioxopyrrolidin-1-yl}acetamido>-3-(3-
hydroxyphenyl)propionate 500 mg of {3-[4-(aminoiminomethyl)benzyl]-2,5-
dioxopyrrolidin-1-yl}acetic acid hydrochloride are coupled
with 400 mg of methyl 3-(R,S)-3-amino-3-(3-
hydroxyphenyl)propionate hydrochloride by the process
described above. After working up and chromatographic
purification, 78 mg of methyl 3-(R,S)-3-<{3-[4-
(aminoiminomethyl)benzyl]-2,5-dioxopyrrolidin-1-
yl}acetamido>-3-(3-hydroxyphenyl)propionate are
obtained.

MS (ES): 467.2 [M+H]$^+$

Example 16

3-(R,S)-3-<{3-[4-(Aminoiminomethyl)benzyl]-2,5-
dioxopyrrolidin-1-yl}acetamido>-3-(3-
hydroxyphenyl)propionate 50 mg of methyl 3-(R,S)-3-<{3-[4-(aminoiminomethyl)
benzyl]-2,5-dioxopyrrolidin-1-yl}acetamido>-3-(3-
hydroxyphenyl)propionate are allowed to stand at room
temperature for 1 h with ml of concentrated hydrochloric
acid. The mixture is then concentrated to dryness in vacuo,
and the residue is taken up in a little water and freeze-dried.
22 mg of 3-(R,S)-3-<{3-[4-(aminoiminomethyl)benzyl]-2,
5-dioxopyrrolidin-1-yl}acetamido>-3-(3-hydroxyphenyl)
propionate are obtained.

MS(ES): 453.1 [M+H]$^+$

Example 17

{3-[4-(Aminoiminomethyl)benzyl]-2,5-
dioxopyrrolidin-1-yl}acetyl-D,L-homophenylalanine 45 mg of {3-[4-(aminoiminomethyl)benzyl]-2,5-
dioxopyrrolidin-1-yl}acetyl-D,L-homophenylalanine
methyl ester are allowed to stand at room temperature for 1
h with 5 ml of concentrated hydrochloric acid. The mixture
is then concentrated to dryness in vacuo, and the residue is
taken up in a little water and freeze-dried. 24 mg of
{3-[4-(aminoiminomethyl)benzyl]-2,5-dioxopyrrolidin-1-
yl}acetyl-D,L-homophenylalanine are obtained.

MS(FAB): 451.2 [M+H]$^+$

Example 18

{3-[4-(Aminoiminomethyl)benzyl]-2,5-
dioxopyrrolidin-1-yl}acetyl-L-tryptophan 204 mg of {3-[4-(aminoiminomethyl)benzyl]-2,5-
dioxopyrrolidin-1-yl}acetyl-L-tryptophan methyl ester are
heated with 10 ml of 6N HCl for 3 min, then the mixture is
evaporated to dryness and the residue is redistilled twice
with water. The residue is taken up in a little water and
freeze-dried. 68 mg of {3-[4-(aminoiminomethyl)benzyl]-2,
5-dioxopyrrolidin-1-yl}acetyl-L-tryptophan are obtained.

MS(FAB): 476.2 [M+H]$^+$

Example 19

{3-[Piperidin-4-yl]-2,5-dioxopyrrolidin-1-yl}acetyl-
L-aspartyl-L-phenylglycine a) Synthesis of ethyl 4-(4-pyridyl)-3,3-
bisethoxycarbonylbutyrate 24.6 g of triethyl 1,1,2-ethanetrlcarboxylate are dissolved
in 900 ml of abs. ethanol and treated in portions with 38.6 g of potassium tert-butoxide. 29.8 g of 4-chloromethylpyridine hydrochloride suspended in 400 ml of abs. ethanol are added to this mixture in portions. It is heated at about 50° C. for 5 h and allowed to stand at room temperature overnight. The precipitate is then filtered off and the filtrate is concentrated in vacuo. The oily residue which remains is chromatographed on silica gel using ethyl acetate. The clean fractions are combined and concentrated to dryness in vacuo. An oil remains which slowly crystallizes.

Yield: 19.7 g
MS (CI): 338 [M+H]$^+$
NMR(CDCl$_3$): 1.25 ppm (m, 9H); 2.84 ppm (s, 2H); 3.40 ppm (s, 2H); 4.20 ppm (m, 6H); 7.08 ppm (dd, 2H); 8.50 ppm (dd, 2H).

b) Synthesis of 4-(4-pyridyl)-3,3-bisethoxycarbonylbutyric acid 8.75 g of ethyl 4-(4-pyridyl)-3,3-bisethoxycarbonylbutyrate are stirred at 50°–60° C. in 500 ml of 6N HCl for 2 h. The mixture is then concentrated in vacuo and allowed to react again at 50°–60° C. with 500 ml of 6N HCl for 2 h. It is then concentrated to dryness in vacuo and redistilled twice using a little toluene. The residue is taken up in a little water and freeze-dried.

Yield: 9.31 g (still contains some triester)
MS(FAB): 310.1 [M+H]$^+$ c) Synthesis of [4-(4-pyridyl)-3,3-bisethoxycarbonylbutyryl]glycine methyl ester 9.27 g of 4-(4-pyridyl)-3,3-bisethoxycarbonylbutyric acid are dissolved in 600 ml of dimethylformamide. 3.69 g of glycine methyl ester hydrochloride, 8.78 g of TOTU and 11.5 ml of N-ethylmorpholine are then added successively. The mixture is stirred for 24 h and the solvent is then stripped off in vacuo. The oily residue is chromatographed on silica gel using ethyl acetate. The fractions containing the product are combined and concentrated.

Yield: 6.6 g
MS(FAB): 381.1 [M+H]$^+$ d) Synthesis of [3-(4-pyridyl)-2,5-dioxopyrrolidin-1-yl]acetic acid 3.58 g of [4-(4-pyridylyl)-3,3-bisethoxycarbonylbutyryl]-glycine methyl ester are refluxed in 1000 ml of conc. HCl for 30 min, then the mixture is concentrated to dryness in vacuo, redistilled five times with toluene and dried in a high vacuum.

Yield: 2.75 g
MS(DCI): 249 [M+H]$^+$ e) Synthesis of [3-(piperidin-4-yl)-2,5-dioxopyrrolidin-1-yl]acetic acid 2.8 g of [3-(4-pyridyl)-2,5-dioxopyrrolidin-1-yl]acetic acid are suspended in 160 ml of acetic acid and hydrogenated in an autoclave at 100° C. and a hydrogen pressure of 150 bar for 24 h using 100 mg of 5% rhodium on carbon as a catalyst. The catalyst is then filtered off and the filtrate is concentrated to dryness in vacuo. The product thus obtained is taken up in a little water and freeze-dried.

Yield: 2.3 g
MS(ES): 255 [M+H]$^+$ f) Synthesis of {3-[(1-tert-butyloxycarbonyl)piperidin-4-yl]-2,5-dioxopyrrolidin-1-yl}acetic acid 100 mg of [3-(piperidin-4-yl)-2,5-dioxopyrrolidin-1-yl]-acetic acid are dissolved in 15 ml of DMF and treated with 87.3 mg of di-tert-butyl carbonate and 51 µl of triethylamine. After 1 h, the solvent is stripped off in vacuo and the residue is partitioned between ether and water. The ether phase is dried over sodium sulphate and then concentrated in vacuo. 120 mg of an oil remain, which is immediately further reacted.

MS (FAB): 377.2 [M+Na]$^+$, 355.3 [M+H]$^+$ g) Synthesis of {3-[(1-tert-butyloxycarbonyl)piperidin-4-yl]-2,5-dioxopyrrolidin-1-yl}acetyl-L-(β-tert-butyl)aspartyl-L-phenylglycine tert-butyl ester 110 mg of {3-[(1-tert-butyloxycarbonyl)piperidin-4-yl]-2,5-dioxopyrrolidin-1-yl}acetic acid are dissolved in 15 ml of DMF and treated successively with 128.5 mg of H-Asp (OtBu)-Phg-OtBu, 101.7 mg of TOTU and 120 µl of N-ethylmorpholine. The mixture is stirred for 24 h and then concentrated to dryness. The oily residue which remains is chromatographed on silica gel using dichloromethane/methanol/water/acetic acid (100:10:1:1). The combined substance-containing fractions are concentrated. 90 mg remain, which are immediately further reacted.

MS(ES): 715 [M+H]$^+$ h) Synthesis of {3-[piperidin-4-yl]-2,5-dioxopyrrolidin-1-yl}-acetyl-L-aspartyl-L-phenylglycine 90 mg of {3-[(1-tert-butyloxycarbonyl)-piperidin-4-yl]-2,5-dioxopyrrolidin-1-yl}acetyl-L-(β-tert-butyl)aspartyl-L-phenylglycine tert-butyl ester are dissolved in 10 ml of trifluoroacetic acid, and the solution is allowed to stand at room temperature for 20 min and is then concentrated to dryness. The residue is redistilled twice with some diethyl ether, dissolved in a little water and the solution is freeze-dried.

Yield: 60 mg
MS(FAB): 503.4 [M+H]$^+$

Example A

Emulsions containing 3 mg of active compound per 5 ml can be prepared according to the following recipe:

| | |
|---|---|
| Active compound | 0.06 g |
| Neutral oil | q.s. |
| Sodium carboxymethylcellulose | 0.6 g |
| Polyoxyethylene stearate | q.s. |
| Pure glycerol | 0.6 to 2 g |
| Aromatizers | q.s. |
| Water (demineralized or distilled) | to 100 ml |

Example B

Tablets can be prepared according to the following formulation:

| | |
|---|---|
| Active compound | 2 mg |
| Lactose | 60 mg |
| Maize starch | 30 mg |
| Soluble starch | 4 mg |
| Magnesium stearate | 4 mg |
| | 100 mg |

Example C

The following composition is suitable for the preparation of soft gelatine capsules containing 5 mg of active compound per capsule:

| | |
|---|---|
| Active compound | 5 mg |
| Mixture of triglycerides from coconut oil | 150 mg |
| Capsule contents | 155 mg |

Example D

The following formulation is suitable for the preparation of sugar-coated tablets:

| | |
|---|---|
| Active compound | 3 mg |
| Maize starch | 100 mg |
| Lactose | 55 mg |
| Sec-calcium phosphate | 30 mg |
| Soluble starch | 3 mg |
| Magnesium stearate | 5 mg |
| Colloidal silicic acid | 4 mg |
| | 200 mg |

Example E

Sugar-coated tablets, containing an active compound according to the invention and another therapeutically active substance:

| | |
|---|---|
| Active compound | 6 mg |
| Propanolol | 40 mg |
| Lactose | 90 mg |
| Maize starch | 90 mg |
| Sec-calcium phosphate | 34 mg |
| Soluble starch | 3 mg |
| Magnesium stearate | 3 mg |
| Colloidal silicic acid | 4 mg |
| | 270 mg |

Example F

Sugar-coated tablets, containing an active compound according to the invention and another therapeutically active substance:

| | |
|---|---|
| Active compound | 5 mg |
| Pirlindol | 5 mg |
| Lactose | 60 mg |
| Maize starch | 90 mg |
| Sec-calcium phosphate | 30 mg |
| Soluble starch | 3 mg |
| Magnesium stearate | 3 mg |
| Colloidal silicic acids | 4 mg |
| | 200 mg |

Example G

Capsules, containing an active compound according to the invention and another therapeutically active substance:

| | |
|---|---|
| Active compound | 5 mg |
| Nicergoline | 5 mg |
| Maize starch | 185 mg |
| | 195 mg |

Example H

Injection solutions containing 1 mg of active compound per ml can be prepared according to the following recipe:

| | |
|---|---|
| Active compound | 1.0 mg |
| Polyethylene glycol 400 | 0.3 mg |
| Sodium chloride | 2.7 mg |
| Water for injection to | 1 ml |

We claim:
1. Heterocycles of the formula I

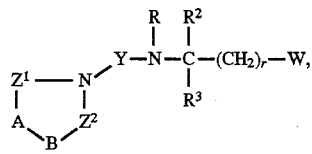

in which $Z^1$ denotes

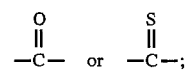

$Z^2$ denotes

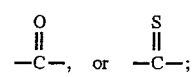

Y denotes —$(CH_2)_m$CO—, where m stands for an integer from 1 to 4, or

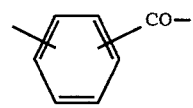

r denotes an integer from 0 to 3;

A denotes —$CHR^1$—, —$NR^1$— or $X^1$—$C_6H_4$—CH=C<;

B denotes —$CH_2$— or —O—;

W denotes —$COW^1$, or tetrazoly;

$W^1$ denotes hydroxyl, $(C_1-C_{28})$-alkoxy, or $(C_6-C_{14})$-aryl-$(C_1-C_8)$-alkoxy;

R denotes hydrogen or $(C_1-C_6)$-alkyl;

$R^1$ denotes —$(CH_2)_p$—$C_6H_4$—$(CH_2)_q$—NH—X or —$(CH_2)_p$—$C_6H_4$—$(CH_2)_q$—C(=NX)—$NH_2$, in which p and q independently of one another stand for a number from 0 to 3;

X denotes hydrogen, $(C_1-C_6)$-alkylcarbonyl, $(C_1-C_6)$-alkoxycarbonyl, $(C_1-C_{18})$-alkylcarbonyloxy-$(C_1-C_6)$-alkoxycarbonyl, $(C_6-C_{14})$-aryl-$(C_1-C_6)$-alkoxycarbonyl, or a radical of the formula II

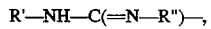

where R' and R" independently of one another stand for hydrogen, $(C_1-C_6)$-alkoxycarbonyl, $(C_1-C_6)$-alkylcarbonyl, $(C_1-C_{18})$-alkylcarbonyloxy-$(C_1-C_6)$ alkoxycarbonyl, or $(C_6-C_{14})$-aryl-$(C_1-C_6)$-alkoxycarbonyl;

$X^1$ denotes —$(CH_2)_q$—NH—X or —$(CH_2)_p$—C(=NX)—$NH_2$, in which p and q stand for a number from 0 to 3;

$R^2$ denotes hydrogen, $(C_1-C_4)$-alkyl or phenyl, where the $(C_1-C_4)$-alkyl and the phenyl can be unsubstituted or mono- or polysubstituted By identical or different radicals from the series hydroxyl, amino, $(C_1-C_4)$-alkoxy, imidazolyl, indolyl, pyrrolidinyl, hydroxypyrrolidinyl, phenyl or halogen;

$R^3$ denotes hydrogen, —CO—N($CH_3$)$R^4$ or —CO—NH—$R^4$;

$R^4$ denotes $(C_1-C_{28})$-alkyl, which can optionally be mono- or polysubstituted by identical or different radicals from the series hydroxyl, hydroxycarbonyl, aminocarbonyl, $(C_6-C_{14})$-aryl-$(C_1-C_8)$-alkoxycarbonyl, amino, $(C_1-C_{18})$-alkoxy, $(C_1-C_{18})$-alkoxycarbonyl, $(C_3-C_8)$-cycloalkyl, or by the radical $R^5$, where $R^5$ denotes optionally substituted $(C_6-C_{14})$-aryl, a radical $R^6$ or a radical $R^6CO$—, where the aryl radical can be mono- or polysubstituted by identical or different radicals from the series $(C_1-C_{18})$-alkyl, $(C_1-C_{18})$-alkoxy, halogen, nitro, amino or trifluoromethyl;

$R^6$ denotes —$NR^7R^8$, —$OR^7$, tetrazolyl, an amino acid side chain, a natural or unnatural amino acid, imino acid, or a dipeptide radical, and also their esters and amides, where free functional groups can optionally be protected by protective groups customary in peptide chemistry;

$R^7$ denotes hydrogen, $(C_1-C_{18})$-alkyl, or $(C_6-C_{14})$-aryl-$(C_1-C_8)$-alkyl;

$R^8$ denotes hydrogen, $(C_1-C_{18})$-alkyl, $(C_6-C_{14})$-aryl or $(C_6-C_{14})$-aryl-$(C_1-C_8)$-alkyl, and their physiologically tolerable salts.

2. Heterocycles according to claim 1, wherein in the formula I

Y denotes —$(CH_2)_mCO$—, where m stands for 1 or 2, or

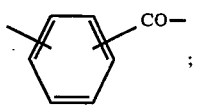

r stands for 1;
W denotes —$COW^1$;
$Z^2$ denotes

$W^1$ denotes hydroxyl, $(C_1-C_4)$-alkoxy, or benzyloxy;
R denotes hydrogen;
$R^1$ denotes —$(CH_2)_p$—$C_6H_4$—$(CH_2)_q$—NH—X or —$(CH_2)_p$—$C_6H_4$—$(CH_2)_q$—C(=NX)—$NH_2$, where p and q independently of one another stand for 0 or 1;
X denotes hydrogen, $(C_1-C_6)$-alkoxycarbonyl, $(C_1-C_6)$-alkylcarbonyl, $(C_1-C_{18})$-alkylcarbonyloxy-$(C_1-C_6)$-alkoxycarbonyl, $(C_6-C_{14})$-aryl-$(C_1-C_6)$-alkoxycarbonyl or a radical of the formula

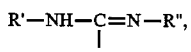

in which R' and R" independently of one another stand for hydrogen, $(C_1-C_6)$-alkylcarbonyl, $(C_1-C_6)$-alkoxycarbonyl, $(C_1-C_{18})$-alkylcarbonyloxy-$(C_1-C_6)$-alkoxycarbonyl or $(C_6-C_{14})$-aryl-$(C_1-C_6)$-alkoxycarbonyl;

$X^1$ denotes —$(CH_2)_q$—NH—X or —C(=NX)—$NH_2$, where q stands for 0 or 1;

$R^2$ denotes hydrogen;

$R^3$ denotes —CO—NH—$R^4$, where —NH—$R^4$ stands for the radical of an α-amino acid, its ω-amino-$(C_2-C_8)$-alkylamide or its $(C_1-C_8)$-alkyl or benzyl ester, or where $R^4$ denotes methyl which is substituted by an amino acid side chain and by a tetrazolyl radical.

3. Heterocycles according to claim 2, wherein $R^3$ denotes —CO—NH—$R^4$, where —NH—$R^4$ stands for the radical of the α-amino acids valine, lysine, phenylalanine, phenylglycine or 4-chlorophenylglycine, their ωamino-$(C_2-C_8)$-alkylamides or their $(C_1-C_8)$-alkyl or benzyl esters.

4. Heterocycles according to claim 3, wherein the $(C_1-C_8)$-alkyl ester of the α-amino acids is the methyl, ethyl, isopropyl, isobutyl or tert-butyl ester.

5. Process for the preparation of compounds of the formula I according to claim 1, wherein a fragment condensation of a compound of the general formula III

with a compound of the general formula IV

is carried out, where the radicals A, B, $Z^1$, $Z^2$, W, Y, R, $R^2$, $R^3$ and r are defined as indicated in claim 1.

6. Pharmaceutical preparation comprising one or more compounds of the formula I according claim 1 and/or one or more physiologically tolerable salts thereof as active compound together with pharmaceutically acceptable excipients and additives and optionally also one or more other pharmacological active compounds.

7. Process for inhibiting platelet aggregation, the metastasis of carcinoma cells or osteoclast binding to the bone surface, which comprises administering to a patient in need thereof an effective dose of a compound of the formula I according to claim 1.

8. Heterocycles according to claim 2 in which $W^1$ denotes a $(C_1-C_4)$-alkoxy radical selected from the group consisting of methoxy, ethoxy, 2-propyloxy, isobutyloxy and tert-butyloxy.

* * * * *

UNITED STATES PATENT AND TRADEMARK OFFICE
CERTIFICATE OF CORRECTION

PATENT NO. : 5,658,935
DATED      : August 19, 1997
INVENTOR(S): Klingler et al.

It is certified that error appears in the above-identified patent and that said Letters Patent is hereby corrected as shown below:

Claim 1, col. 22, line 35 "tetrazoly" should read --tetrazolyl--;

Claim 1, col. 22, line 59, "By" should read --by--.

Signed and Sealed this

Twenty-first Day of April, 1998

Attest:

BRUCE LEHMAN

*Attesting Officer*    *Commissioner of Patents and Trademarks*